US009480530B2

(12) United States Patent
Allehiany

(10) Patent No.: US 9,480,530 B2
(45) Date of Patent: Nov. 1, 2016

(54) CONTAINER FOR THE SAFE COLLECTION AND DISPOSAL OF USED MEDICAL SHARPS

(71) Applicant: Umm Al-Qura University, Makkah (SA)

(72) Inventor: Obaidullah H. S. Allehiany, Makkah (SA)

(73) Assignee: Umm Al-Qura University, Makkah (SA)

( * ) Notice: Subject to any disclaimer, the term of this patent is extended or adjusted under 35 U.S.C. 154(b) by 295 days.

(21) Appl. No.: 14/255,541

(22) Filed: Apr. 17, 2014

(65) Prior Publication Data
US 2015/0297298 A1    Oct. 22, 2015

(51) Int. Cl.
| | | |
|---|---|---|
| B65D 83/02 | (2006.01) |
| A61B 19/02 | (2006.01) |
| B65D 25/00 | (2006.01) |
| B65D 25/28 | (2006.01) |
| B65D 43/16 | (2006.01) |
| B65D 43/22 | (2006.01) |
| B65D 83/00 | (2006.01) |

(52) U.S. Cl.
CPC ........... *A61B 19/0288* (2013.01); *A61B 50/36* (2016.02); *A61B 50/362* (2016.02); *B65D 25/005* (2013.01); *B65D 25/2802* (2013.01); *B65D 43/16* (2013.01); *B65D 43/22* (2013.01); *B65D 83/0038* (2013.01); *B65D 83/02* (2013.01); *A61B 2050/0056* (2016.02); *A61B 2050/0067* (2016.02); *B65D 2525/282* (2013.01)

(58) Field of Classification Search
CPC .. A61B 19/02; A61B 19/0288; B65D 25/00; B65D 25/005; B65D 25/28; B65D 25/2802; B65D 43/16; B65D 43/22; B65D 83/0038; B65D 83/02; B65D 2525/282; Y10S 220/908; A61M 5/3205
USPC ............... 206/363, 366, 370, 438; 220/908; 221/208, 209, 247, 250; 232/43.1–43.3
See application file for complete search history.

(56) References Cited

U.S. PATENT DOCUMENTS

| | | | | |
|---|---|---|---|---|
| 4,332,348 A * | 6/1982 | Nordin | ...................... | G07F 9/06 232/43.3 |
| 4,809,850 A * | 3/1989 | Laible | ................ | A61B 19/0288 206/366 |
| 5,076,458 A * | 12/1991 | Weiner | .................... | B65F 1/006 232/43.2 |
| 5,172,808 A | 12/1992 | Bruno | | |
| 5,201,418 A * | 4/1993 | Hanlon | ............... | A61M 5/3205 206/366 |
| 5,411,193 A | 5/1995 | Culp | | |
| 5,590,774 A * | 1/1997 | Roberts | ............ | A61B 17/06161 206/366 |
| 5,791,471 A | 8/1998 | Radmand | | |
| 5,829,588 A * | 11/1998 | Bloomfield | ............... | B65F 1/10 206/366 |
| 7,235,063 B2 | 6/2007 | D'Antunio et al. | | |

(Continued)

*Primary Examiner* — Bryon Gehman
(74) *Attorney, Agent, or Firm* — Dennis H. Lambert

(57) ABSTRACT

A container into which used sharps can be deposited immediately following their use and carried to a second container into which the used sharps can be dumped for subsequent disposal without having to directly handle the sharps following their use. A top wall is normally latched closed and is opened to deposit used sharps into the container. A normally closed end wall is opened so that the used sharps can be dumped from the container. The container has a pistol-type grip for carrying it, and in a first embodiment a rearwardly biased pusher is slidably mounted in the container and moved forwardly by depressing a trigger on the grip. In a second embodiment, the pusher is biased forwardly and is latched in a rearward position. The trigger is connected with the latch to release it so the pusher can move forwardly.

9 Claims, 5 Drawing Sheets

(56) References Cited

U.S. PATENT DOCUMENTS 7,789,230 B2    9/2010  Klein
8,162,139 B2 *  4/2012  Iske .................... A61M 5/3205
                                                206/363
8,235,883 B2 *  8/2012  Iske .................... A61M 5/3205
                                                206/363
8,434,616 B2    5/2013  Erickson et al.

* cited by examiner

CONTAINER FOR THE SAFE COLLECTION AND DISPOSAL OF USED MEDICAL SHARPS

FIELD OF THE INVENTION

This invention relates generally to the disposal of used medical sharps, and particularly to a reusable container for the safe collection of used sharps at a point of use and from which the used sharps may be discharged into a receptacle for transporting the used sharps to a suitable disposal site.

BACKGROUND ART

Used medical sharps pose a danger to medical professionals and others who must handle the used sharps due to the danger of being cut or pricked with the used sharps, which may be contaminated with various pathogens, including human immunodeficiency virus (HIV), hepatitis or other infectious and/or contagious diseases. Accidental needle sticks with contaminated needles accounts for one of the most serious health risks to medical personnel, with hundreds of thousands of accidental sticks officially reported.

Because of this danger, health care regulations have mandated the safe disposal of used sharps. Hospitals and clinics use special containers dedicated to the disposal of used needles and other sharps. The primary function of these sharps containers is to provide a rigid enclosure into which used sharps are deposited, reducing the exposure of practitioners to contaminated used sharps and protecting individuals from becoming injured by an exposed used sharp. These containers provide a safe way to store used sharps during transport and disposal by industrial waste collectors. In most instances, these sharps containers are permanently attached to a surface in the room where the sharps are used.

Medical practitioners are most vulnerable to a needle stick at two critical times during patient care activities: immediately following use of sharps in a medical procedure; and during post-operative clean-up after the activity is concluded. For instance, when a needle is withdrawn following a procedure, the practitioner's attention is divided between needle/syringe disposal and continued patient care, which may not leave a hand free, or leave only one hand free, for the practitioner to properly dispose of the used needle. Accordingly, the used needle will either be handed to an assistant for disposal or simply laid down for subsequent retrieval during clean-up. Either approach requires the used needle to be handled more than once, increasing the risk of injury.

U.S. Pat. No. 5,411,193 to Culp discloses a portable intermediate containment device that is mounted on the practitioner so that it is always at hand during a medical procedure to receive used medical objects such as needles, syringes, scalpels, probes, swabs, and the like for safe conveyance to a permanent disposal container. The Culp device is intended for single use and does not have provision for emptying it of used sharps.

U.S. Pat. No. 5,172,808 to Bruno discloses a tubular holder into which used needles may be placed for secure handling until the holders and used needles contained therein are placed in a disposal container for transporting the used sharps to a suitable disposal site. The Bruno device is intended for single use and does not have provision for emptying it of used sharps.

U.S. Pat. No. 7,971,715 to Fernandes, et al. discloses a disposable container for used medical sharps, wherein the container has a transparent viewing window 16b and an auditory and/or visual alarm to indicate when the container is full and needs to be replaced. This container is not intended to be emptied into a second container and reused.

Applicant is not aware of any reusable container for temporary receipt of used sharps at the point of use and subsequent deposit of the used sharps into a second container for transport to a suitable disposal site.

SUMMARY OF THE INVENTION

The present invention comprises a reusable container into which used sharps can be deposited immediately following their use and carried to a second container into which the used sharps can be dumped for subsequent disposal without having to directly handle the sharps following their use. The container comprises a housing having a bottom wall, a front wall, a back wall, a top wall, a rearward end and a forward end. The top wall is hinged to the back wall for pivotal movement between an open position to enable deposit of used sharps into the container and a closed position to prevent an accidental stick with the used sharps. First latch means is engaged between the top wall and the front wall to latch the top wall closed. A forward end wall is mounted on the housing forward end for pivotal movement between a closed position and an open position. In one embodiment the forward end wall is pivotally attached to the bottom of the housing, and in another embodiment it is pivotally attached to the top of the housing. Second latch means is engaged between the forward end wall and the housing to latch the forward end wall closed. A pistol grip type handle is attached to the housing rearward end for carrying the container.

In a preferred embodiment, a pusher inside the container pushes the used sharps toward the open end of the container when the forward end wall is opened. In one embodiment the pusher is spring biased to a rearward position and first means is connected between the trigger and the pusher to move the pusher toward the open end of the container when the trigger is operated. In another embodiment, the pusher is latched in a rearward position by third latch means and pneumatic means is connected with the pusher to move it toward the open end of the container to dump used sharps from the container when the trigger is operated to disengage the third latch means. Second means is connected between the trigger and the third latch means to disengage the third latch means when the trigger is depressed.

The container preferably is made of a suitable material such as plastic or metal resistant to penetration by needles and other sharps. In a preferred embodiment, the top lid is transparent or at least has a transparent window so that the interior of the container can be observed to determine when the container is full or nearly full of used sharps. In a further preferred form of the invention a ledge extends rearwardly over the pistol grip to protect the hand of a user and prevent accidental sticks by used sharps being deposited into the container.

BRIEF DESCRIPTION OF THE DRAWINGS

The foregoing, as well as other objects and advantages of the invention, will become apparent from the following detailed description when taken in conjunction with the accompanying drawings, wherein like reference characters designate like parts throughout the several views, and wherein.

DETAILED DESCRIPTION OF THE PREFERRED EMBODIMENTS

Figure 1:
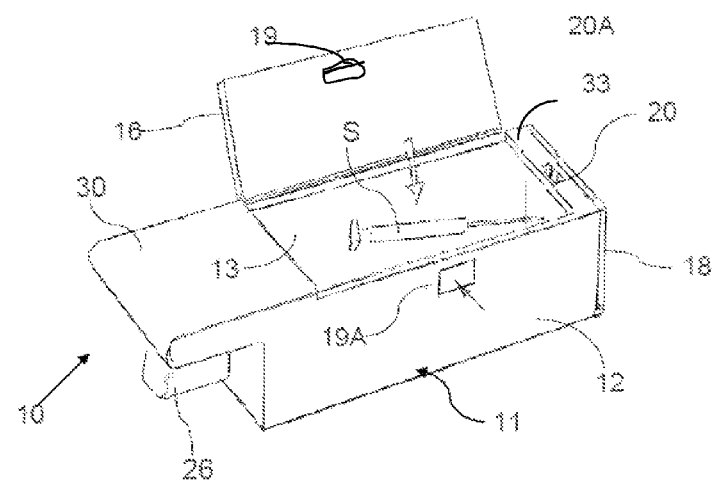
FIG. 1 is a top isometric view of a first form of sharps disposal container according to the invention, with the top lid shown in an open position and a used syringe being deposited into the container.
Figure 2:
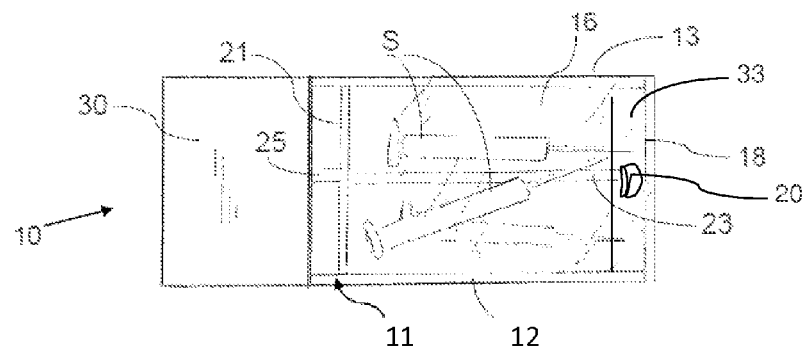
FIG. 2 is a top plan view of the container of FIG. 1, illustrating the transparency of the lid and showing used sharps in the container.
Figure 3:
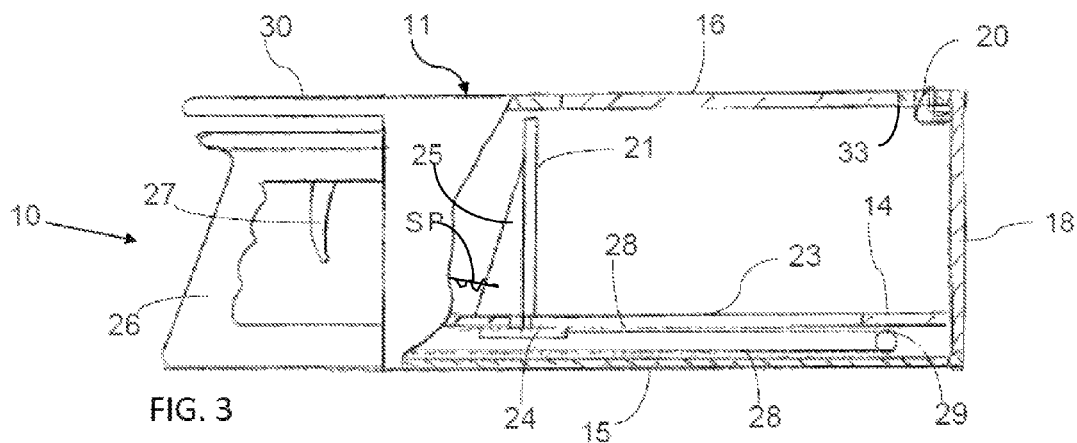
FIG. 3 is an enlarged side view of the container of FIGS. 1-2, with portions broken away to show some of the operative components.
Figure 4:
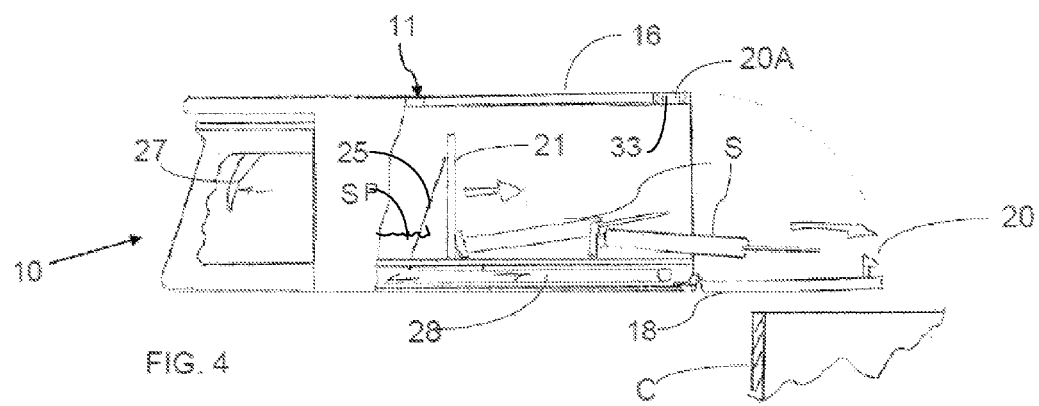
FIG. 4 is a side view of the container of FIGS. 1-3, with portions broken away, showing the end wall open and the pusher being pushed forwardly to dump used syringes from the container into a second container.
Figure 5:
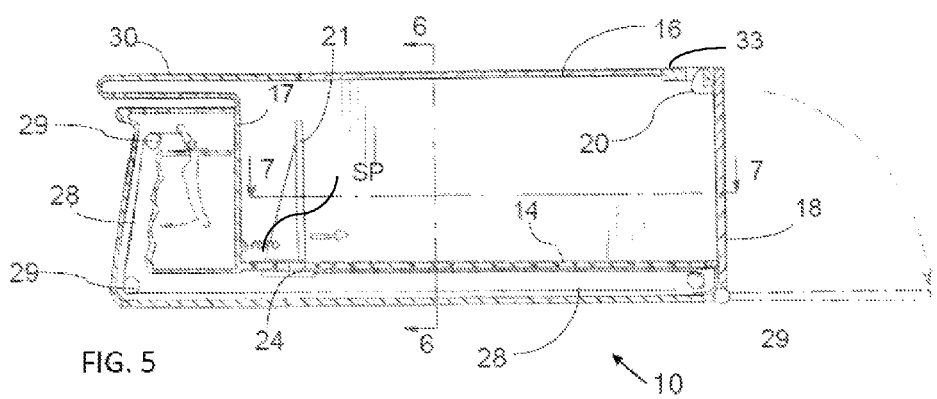
FIG. 5 is a slightly enlarged longitudinal sectional view of the container of FIG. 4, with the lid and end wall closed and showing details of the trigger operating mechanism for unlatching the lid and end wall and pulling the pusher forward in the container.
Figure 6:
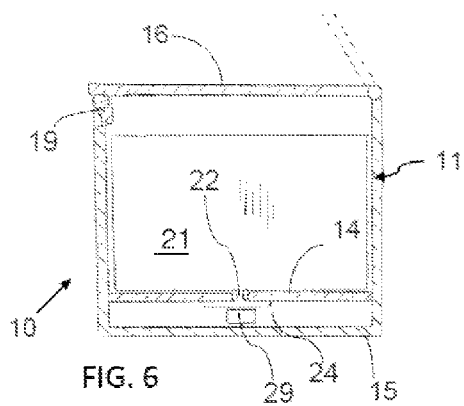
FIG. 6 is a transverse sectional view taken along line 6-6 in FIG. 5.
Figure 7:
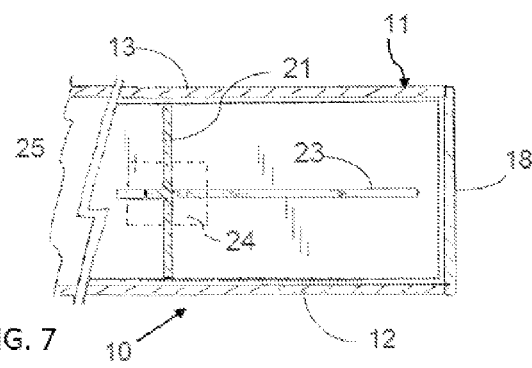
FIG. 7 is a sectional view taken along line 7-7 in FIG. 5.

A first form of reusable container for temporary receipt of used sharps and subsequent discharge of them into a second container C (see FIG. 4) for transport to a suitable disposal site is indicated generally at 10 in FIGS. 1-7. The container comprises a generally rectangularly shaped housing 11 having a front wall 12, a back wall 13, an inner bottom wall 14, an outer bottom wall 15, an openable lid 16 pivotally attached to the top edge of back wall 13, a rearward end wall 17, and an openable forward end wall 18 pivotally attached at its bottom edge to the forward end of the outer bottom wall 15. A first latch means 19 at the front edge of the lid 16 engages in an opening 19A in the wall 12 to hold the lid closed until it is desired to open it to place used sharps "S" into the container, and a second latch means 20 at the top edge of the end wall 18 engages in an opening 20A in a bar 33 extending across the end of the housing to hold the end wall closed until it is desired to open the end wall to dump the used sharps "S" into a second container C for transport to a suitable disposal site. In the embodiment shown, the latches 19 and 20 are released by using the thumb or finger to push the respective latches inwardly until they are disengaged from the edges of the associated holes 19A or 20A in the adjacent housing part.

In the preferred embodiment, a pusher 21 is mounted to the inner bottom wall 14 for sliding movement toward the forward end of the container to push used sharps "S" from the container through the open end when the end wall 18 is opened. The pusher is generally rectangular and is sized to extend across the width of the housing between the front and back walls 12 and 13, and also to extend substantially the height of the housing between the inner bottom wall 14 and lid 16. An extension 22 on the bottom of the pusher extends through a slot 23 in the inner bottom wall 14 and is connected with a stabilizing base 24 below the wall 14 to help maintain the pusher in an upright position. A reinforcing brace 25 may be provided on the back side of the pusher if desired or necessary. A spring "SP" connected between the pusher and the rear wall 17 comprises a first biasing means for urging the pusher 21 toward the rearward end of the container. Accordingly, following discharge of used sharps from the container and release of the trigger, the spring will return the pusher to its position near the rearward end of the housing.

A pistol grip 26 for handling the container is attached to the rearward end wall 17, and a trigger 27 on the pistol grip is connected to the pusher by a first means to pull the pusher toward the forward end of the housing when the trigger is depressed. In this embodiment, the first means comprises a wire or cable 28 threaded over guides 29 and connected at one end to the trigger and at the other end to the stabilizing base 24 on the pusher.

A ledge 30 projects rearwardly from the rearward end of the housing and over the pistol grip to protect the hand of the user against accidental sticks from used sharps "S" being deposited into the container.

Figure 8:
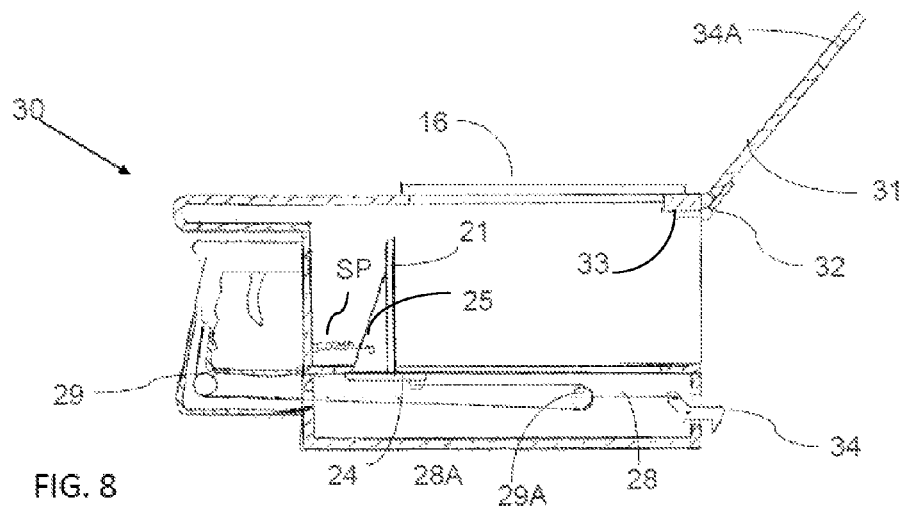
FIG. 8 is a side view in longitudinal section of a second form of sharps disposal container according to the invention, wherein the end wall is pivoted mounted at its top edge rather than its bottom edge as in the previous embodiment.
Figure 9:
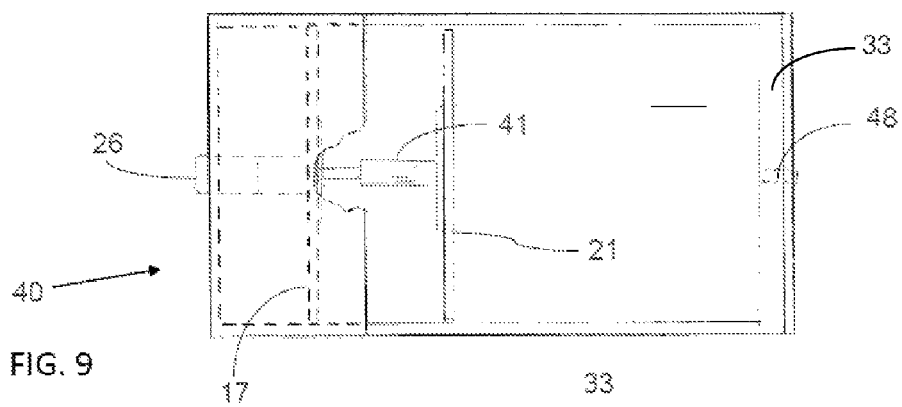
FIG. 9 is a plan view of the container of FIG. 8, showing the transparency of the top lid.
Figure 10:
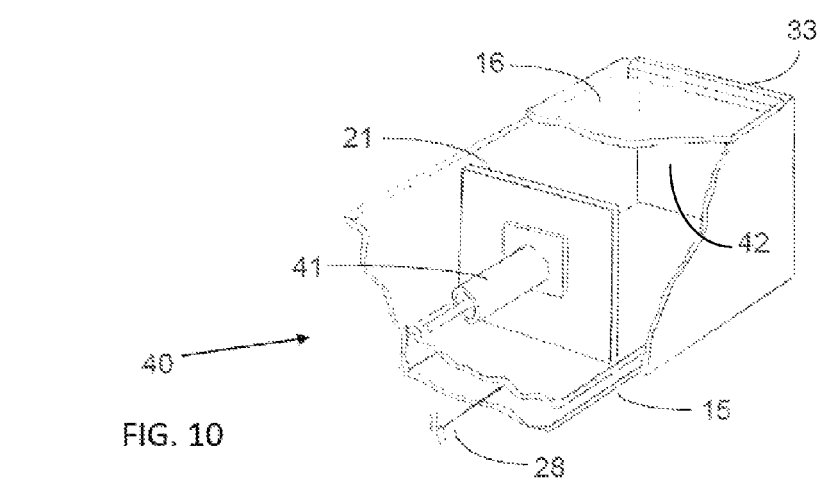
FIG. 10 is a fragmentary isometric view of the container of FIGS. 8 and 9, taken from the rearward end of the container.

A second embodiment is indicated generally at 30 in FIG. 8. In this form of the invention, the end wall 31 is pivotally attached by a spring hinge 32 at its top edge to a bar 33 extending across the top of the forward end of the housing. The end wall 31 is normally biased to an open position as shown in FIG. 8 by the spring hinge 32 and is held in its closed position by a latch 34 at the bottom of the housing engaged in an opening 34A in the bottom edge of the wall 31. The latch is disengaged by depressing the trigger, which is connected with the latch via a wire or cable 28 threaded over guides 29. A second wire 28A threaded over guide 29A is connected with the base 24 on pusher 21 to pull the pusher toward the open end of the housing when the wall 31 is in opened position as shown in FIG. 8.

Figure 11:
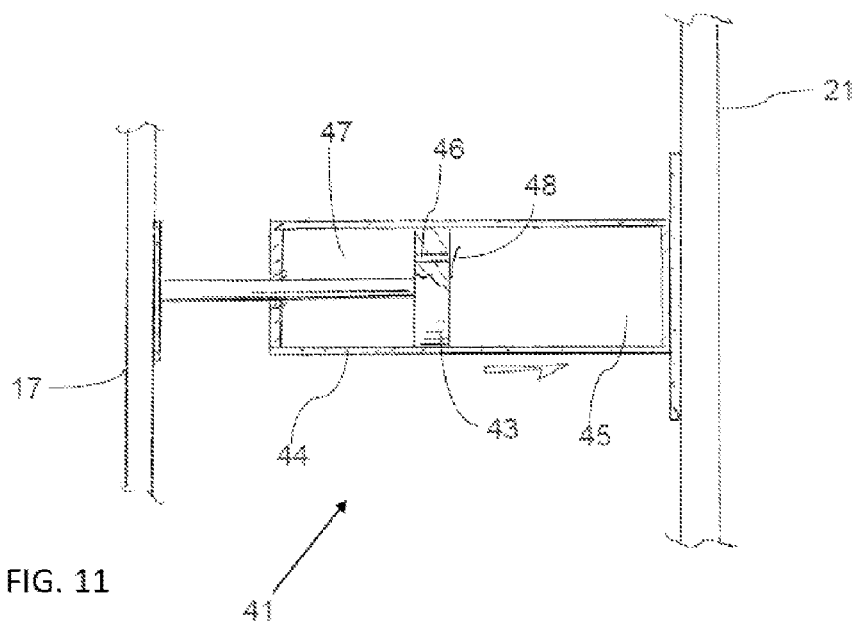
FIG. 11 is a greatly enlarged fragmentary plan view of the pneumatic mechanism for moving the pusher toward the forward end of the container to push used sharps from the container.

A third embodiment is indicated generally at 40 in FIGS. 9-12. In this form of the invention, a pneumatic pressure means 41 is connected between end wall 17 and pusher 21 to urge the pusher toward the forward end of the container. As seen in FIG. 11, the pressure means comprises a piston 43 reciprocal in a cylinder 44, and defining with the cylinder a pressure chamber 45. In the particular example shown, the piston is connected with rearward wall 17 and the cylinder is connected with the pusher 21, although these parts could be reversed. A fluid medium comprising air or other compressed gas is trapped in chamber 45. Because the position of the piston is fixed relative to wall 17, the compressed fluid in chamber 45 biases the cylinder and thus the pusher toward the forward end of the housing. As the cylinder 44 and attached pusher 21 move forwardly under the influence of the compressed fluid in chamber 45, the volume of chamber 45 increases and the pressure thus decreases, avoiding too rapid movement of the pusher. If necessary, a bleed port 46 can be provided through the piston to enable flow of fluid from the chamber 47 at the rear of the piston to the chamber 45 when the pusher is returned to its ready position shown in FIG. 12. A valve 48 controls flow of pressure medium through the port 46 to prevent equalization of pressure on opposite sides of the piston but, if necessary, to enable flow of fluid from chamber 47 to chamber 45 when the pusher is returned to its latched position.

Figure 12:
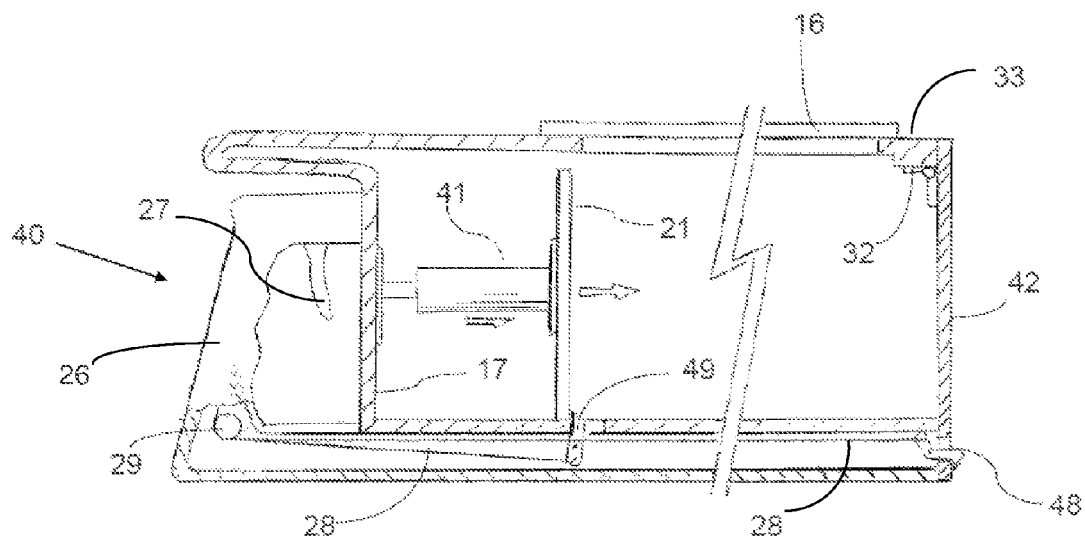
FIG. 12 is a longitudinal sectional view of the container of FIGS. 9-11, showing the latch for holding the pusher in its rearward position.
Figure 13:
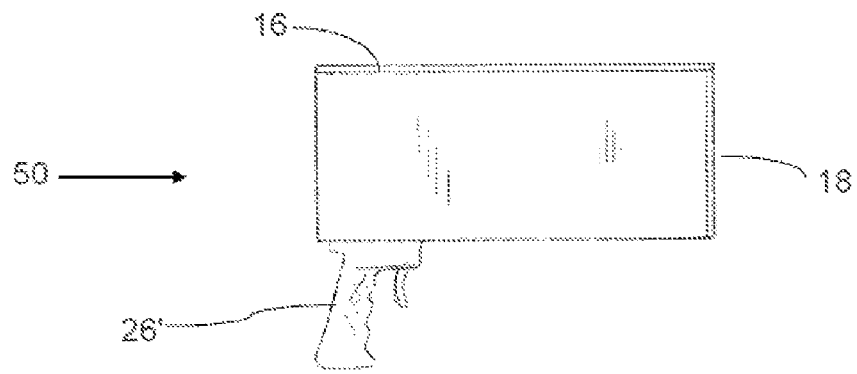
FIG. 13 is a side view in elevation of a third form of sharps disposal container according to the present invention, wherein the pistol grip and trigger are positioned beneath the rearward end of the container.
Figure 14:
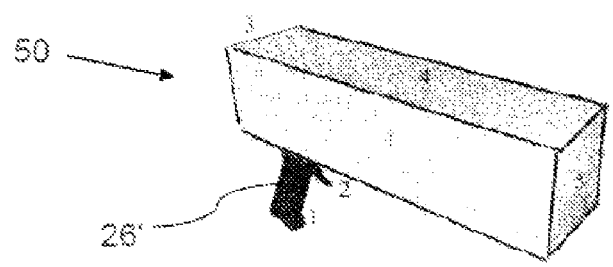
FIG. 14 is a top isometric view of the container of FIG. 13, showing the top lid and end wall in closed position.
Figure 15:
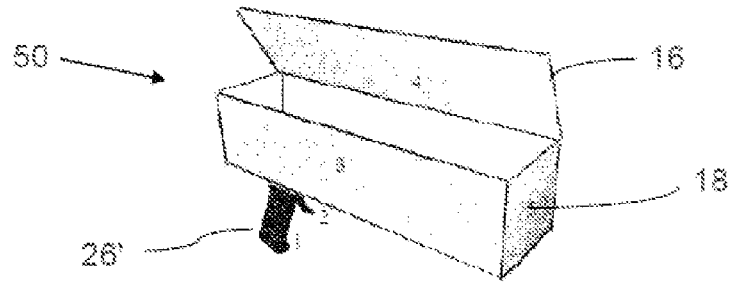
FIG. 15 is a top isometric view of the container of FIG. 14, showing the top lid in opened position and the end wall closed.
Figure 16:
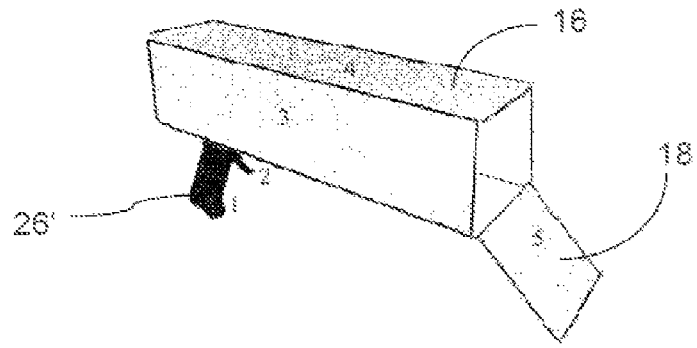
FIG. 16 is a top isometric view of the container of FIG. 14, showing the top lid closed and the end wall in opened position.

The wall 42 is hinged at its top edge to bar 33 extending across the top of the forward end of the housing and is biased to an upwardly pivoted open position by a spring hinge 32 as in the previous embodiment. The wall 42 is latched in a downwardly pivoted closed position as shown in FIG. 12 by a latch 48, and the pusher 21 is held in a rearward position against the bias of pressure means 41 by a third latch means 49 engaged with the bottom edge of the pusher. Second means is connected between the trigger and the third latch means to release the third latch means when the trigger is depressed. In the example shown, the first means comprises a wire or cable 28 connected between the trigger 27 and latch 48 to release the latch when the trigger is depressed, enabling the spring hinge 32 to pivot the wall 42 upwardly to open the forward end of the housing. The second means comprises a wire or cable 28 connected between the trigger and the third latch means 49 to release the latch when the trigger is depressed, enabling the pressure means 41 to move the pusher 21 toward the open forward end to push used sharps out of the container. After the container has been emptied, it can be readied for reuse by moving the pusher rearwardly until the latch 49 is again engaged with the bottom edge of the pusher to hold it in its rearward position, and the wall 42 can be pivoted downwardly to again engage the latch 48. Top wall or lid 16 is releasably latched in a closed position as in the first embodiment described above.

In a variation (not shown) of the third embodiment, a coil spring could be provided in chamber 45 instead of the compressed air or other gas to urge the pusher 21 toward the forward end of the housing. In that case, valve 48 would be omitted but a restricted port 46 could be provided through the piston to regulate the rate of flow of fluid between chambers 44 and 45 and thus regulate the relative speed of movement between the piston and cylinder. The operation would otherwise be essentially the same as in the third embodiment discussed above.

A fourth embodiment is indicated generally at 50 in FIGS. 13-16. This embodiment is constructed and functions essentially the same as the first embodiment described above, except that the pistol grip 26' and associated trigger are mounted on the bottom of the housing rather than on the rearward end as in the first embodiment.

The sharps container of the invention provides a safe and efficient way for medical professionals and other practitioners to dispose of used sharps immediately following their use. Used sharps can be dropped directly into the container without unnecessary handling and exposure to the contaminated sharps, and closure of the lid 16 following deposit of the used sharps completely encloses the sharps to prevent accidental contact with them. Reopening of the lid to deposit further used sharps is done externally of the container without exposure to the used sharps already in the container. When all sharps that have been used in a particular procedure have been placed in the container, or the container is full, it is carried to a receptacle for use in transporting used sharps to a suitable disposal site, the trigger depressed to open the end wall, and the used sharps dumped out into the receptacle. Depression of the trigger also moves the pusher toward the open end of the container to push the used sharps out.

While particular embodiments of the invention have been illustrated and described in detail herein, it should be understood that various changes and modifications may be made in the invention without departing from the spirit and intent of the invention as defined by the appended claims.

What is claimed is:

1. A container into which used sharps can be deposited immediately following their use and carried to a second container into which the used sharps can be dumped for subsequent disposal without having to directly handle the sharps following their use, comprising:
   a housing having a bottom wall, a front wall, a back wall, a top wall, a rearward end closed by a rearward end wall, and a forward end closed by a forward end wall;
   said top wall being hinged to the back wall for pivotal movement between a closed position and an open position;
   said forward end wall being hinged to the housing forward end for pivotal movement between a closed position and an open position;
   first latch means engaged between said top wall and said front wall to latch the top wall closed, said top wall being openable to enable deposit of used sharps into the container and then latched closed to encase the used sharps in the container and prevent an accidental stick with the used sharps;
   second latch means engaged between said forward end wall and said housing forward end to latch the forward end wall closed, said forward end wall being openable to enable the used sharps to be dumped from the container; and
   a pusher slidably mounted in said container for movement from said rearward end toward said forward end to push used sharps from the container when said forward end wall is open.

2. A container as claimed in claim 1, wherein:
   said forward end wall is hinged at a bottom edge thereof to the bottom wall of said housing.

3. A container as claimed in claim 2, wherein:
   a pistol grip type handle is attached to the housing rearward end for carrying the container;
   a depressible trigger is carried by said handle;
   spring means is connected with the pusher to bias it toward the rearward end of the housing; and
   means is connected between said trigger and said pusher to pull said pusher against the bias and toward the forward end of said container when the trigger is depressed.

4. A container as claimed in claim 1, wherein:
   said second latch means is at a bottom edge of said forward end wall, and said forward end wall is hinged at a top edge thereof to the top of said housing by a spring hinge that biases said forward end wall upwardly when the second latch means is released.

5. A container as claimed in claim 4, wherein:
   a pistol grip type handle is attached to the housing rearward end for carrying the container;
   a depressible trigger is carried by said handle;
   spring means is connected with the pusher to bias it toward the rearward end of the housing;

means is connected between said trigger and said pusher to pull said pusher against the bias and toward the forward end of said container when the trigger is depressed; and said trigger is connected with said second latch means to disengage said second latch means when said trigger is depressed to enable said forward end wall to open so that said used sharps can be dumped from the container.

6. A container as claimed in claim 1, wherein:

pneumatic means biases the pusher toward the forward end of the housing;

third latch means engages said pusher to hold it in place against the bias of said pneumatic means;

a handle is attached to the housing rearward end for carrying the container;

a depressible trigger is carried by said handle; and means is connected between said trigger and said third latch means to release said third latch means so that said pneumatic means can move said pusher toward the forward end of said container when the trigger is depressed.

7. A container as claimed in claim 6, wherein:

the pneumatic means comprises a piston reciprocal in a cylinder, said piston and cylinder defining a pressure chamber containing a fluid under pressure.

8. A container as claimed in claim 7, wherein:

the piston is attached to the rearward end wall of the housing and is fixed against movement; and the cylinder is attached to the pusher and moves toward the forward end of the housing to move the pusher toward the forward end of the housing when the third latch means is released.

9. A container as claimed in claim 8, wherein:

said trigger is connected with said second latch means to disengage said second latch means when said trigger is depressed to enable said forward end wall to open so that the used sharps can be pushed from the container by said pusher.

\* \* \* \* \*